United States Patent [19]

Matsuo et al.

[11] 4,376,785
[45] Mar. 15, 1983

[54] CYCLOPROPANECARBOXYLATES AND A LOW FISH TOXIC INSECTICIDE AND/OR ACARICIDE CONTAINING THEM

[75] Inventors: Noritada Matsuo, Itami; Masachika Hirano, Osaka, both of Japan

[73] Assignee: Sumitomo Chemical Company, Limited, Osaka, Japan

[21] Appl. No.: 272,045

[22] Filed: Jun. 9, 1981

[30] Foreign Application Priority Data

Jun. 19, 1980 [JP] Japan .................................. 55-83474
Dec. 29, 1980 [JP] Japan ................................. 55-185574

[51] Int. Cl.³ ...................... A01N 53/00; C07C 121/75
[52] U.S. Cl. .............................. 424/304; 260/465 D; 260/465 F; 568/441
[58] Field of Search ....................... 260/465 D, 465 F; 424/304; 568/441

[56] References Cited

U.S. PATENT DOCUMENTS

| | | | |
|---|---|---|---|
| 4,179,575 | 12/1979 | Martel et al. | 562/506 |
| 4,199,596 | 4/1980 | Fuchs et al. | 424/304 |
| 4,224,227 | 9/1980 | Martel et al. | 260/347.4 |
| 4,242,357 | 12/1980 | Fuchs et al. | 424/282 |
| 4,279,920 | 7/1981 | Fuchs et al. | 424/282 |
| 4,303,672 | 12/1981 | Hirano et al. | 424/304 |

FOREIGN PATENT DOCUMENTS

| | | |
|---|---|---|
| 2805226 | 8/1978 | Fed. Rep. of Germany . |
| 2380247 | 9/1978 | France . |
| 2380248 | 9/1978 | France . |
| 2450249 | 9/1980 | France . |
| 1549462 | 8/1979 | United Kingdom . |
| 1549463 | 8/1979 | United Kingdom . |
| 1565932 | 4/1980 | United Kingdom . |
| 1565933 | 4/1980 | United Kingdom . |
| 2044765 | 10/1980 | United Kingdom . |

*Primary Examiner*—Dolph H. Torrence
*Attorney, Agent, or Firm*—Stevens, Davis, Miller & Mosher

[57] ABSTRACT

The present invention relates to cyclopropanecarboxylates of the formula (I), wherein R and X may be same or different, each is a chlorine or bromine atom, and their production and use as an insecticide and/or acaricide.

8 Claims, No Drawings

CYCLOPROPANECARBOXYLATES AND A LOW FISH TOXIC INSECTICIDE AND/OR ACARICIDE CONTAINING THEM

The present invention relates to cyclopropanecarboxylates of the formula (I),

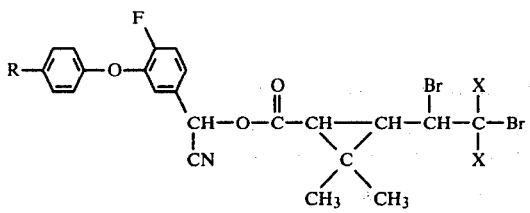

wherein R and X may be same or different, each is a chlorine or bromine atom, their production and an insecticide and/or acaricide containing them as an active ingredient.

Insecticides and/or acaricides are essential materials to maintain high levels of agricultural production by exterminating various insects doing damage to agricultural crops.

Since many of infectious diseases are carried by insects, exterminating the insects is very effective in preventing the diseases from spreading, and for this purpose the use of insecticides is the most effective means. Consequently, the role of insecticides in maintaining a high living standard for mankind from now to future is very great. Many superior insecticides have been invented in order to achieve this object and used in various fields with a good result. Organo-chlorine insecticides such as BHC and DDT were however markedly limited in use, because they generated insects resistant thereto and caused various problems such as environmental pollution and toxicity to organisms out of tartet. Also, this problem of resistant insects is now becoming serious in the fields wherein organo-phosphate or carbamate type insecticides are used in place of the organo-chlorine insecticides. Under these circumstances, development of novel and more superior insecticides is eagerly desired. In order that insecticides may be superior, it is natural that they should have a strong insecticidal activity, but in addition to this, what is now strongly demanded of them is a low toxicity to organisms out of target such as mammals, no persistency and little environmental pollution. Natural pyrethrin is low in toxicity to mammals and easily decoposed in outdoor conditions, so that it possesses a part of the aforesaid properties required for insecticides. But its insecticidal activity is relatively low as compared with that of the organophosphates and carbamates, and besides it is poor in residual effect because of too rapid decomposition and also is expensive. Consequently, the use of natural pyrethrin is limited to such fields as household insecticides. Many studies have been made to make up for these drawbacks of natural pyrethrin and as a result, some superior synthetic pyrethroid insecticides have been developed. Of these pyrethroid compounds, particularly, those described in Literature (1): M. Elliott et al., Nature, 248, 710 (1974), Literature (2): U.K. Pat. No. 413,491 and Literature (3): U.S. Pat. No. 3,996,244 have the following characteristics:

(1) Insecticidal activity is outstandingly high and of rapid effect.

(2) They are rich in residual effect but have no environmental persistency unlike organo-chlorine insecticides.

(3) Toxicity to mammals is relatively low.

(4) Insecticidal activity against insects resistant to organo-phosphates and carbamates is also high.

Consequently, studies on a worldwide scale are now being made in order to put these synthetic pyrethroids to practical use, and in some districts where the spreading of resistant insects is becoming serious, the actual use of them has already begun. But, as shown in Literature (4): J. Miyamoto, Environmental Health Perspectives, Vol. 14, 15 (1976), pyrethroid insecticides including natural pyrethrins generally exhibit a strong toxicity to fishes. Of all the applications of insecticides, by he way, extermination of insects in paddy field and aquatic insects (e.g. mosquito larvae, gnat larvae) and spraying by air over an area wherein lakes, ponds or rivers are present, occupy not a small proportion. In such application as this, it is naturally expected that the above superior synthetic pyrethroid insecticides will be limited in use because of their toxicity to fishes. In this respect, the toxicity to fishes of pyrethroid may be considered as a serious problem to be improved.

On the basis of the thought that an insecticide will make one great step towards the so-called ideal one if there is success in developing compounds which combine the foregoing strong points of the pyrethroid insecticides and a low toxicity to fishes, the inventors made an extensive study and as a result, found that the present compounds of the formula (I) have the characteristics which meet the foregoing objects. The inventors thus attained the present invention.

The present compounds of the formula (I) have a high insecticidal activity and a high residual effect against the insects described below, and besides they are markedly low in toxicity to fishes (e.g. carp, killifishes) and mammals including mice and rats. Consequently, they are particularly useful for exterminating aquatic insects living in paddy fields, ponds, lakes, rivers and woods and forests.

Next, specific examples of insects to which the compounds of the present invention are applied particularly effectively, will be given.

1. Hemiptera:
   (1) Delphacidae (planthoppers): for example, whitebacked planthopper (*Sogatella furcifera*), brown planthopper (*Nilaparvata lugens*), smaller brown planthopper (*Lacodelphax striatellus*)
   (2) Deltocephalidae (leafhoppers): for example, green rice leafhopper (*Nephotettix cincticeps*), green leafhopper (*Tettigella viridis*), zagzag-striped leafhopper (*Inazuma dorsalis*)
   (3) Aphididae (aphids): for example, grain aphid (*Rhopalosiphum padi*)
   (4) Pentatomidae (bugs): for example, common green Stink bug (*Nezara antennata*), white-spotted bug (*Eysarcaris ventralis*)

2. Lepidoptera:
   For example, spruce bud worm (*Archips fumiferana*), rice stem borer (*Chilo suppressalis*), grass leaf roller )*Cuaphalocrocis medinalis*), wax moth (*Galleria mellonella*), pine caterpiller (*Dendrolimus spectabilis*), tent caterpiller (*Malacosoma neustria*)

3. Coleoptera:
   For example, rice leaf beetle (*Oulema oryzae*), rice plant weevil (*Echinocoemus squameus*)

4. Diptera:

For example, yellow fever mosquito (*Aedes aegypti*), malaria mosquito (*Aedes aegypti*), malaria mosquito (*Anopheles sp.*), northern house mosquito (*Culex pipiens pallens*), rice leaf miner (*Agromyza oryzae*).

5. Orthoptera:

For example, short-winged rice grasshopper (*Oxya yezoensis*)

6. Acarina:

For example, carmine mite (*Tetranychus cinnabarinus*), two-spotted spider mite (*Tetranychus urticae*), sugi spider mite (*Oligonychus hondoensis*), citrus red mite (*Panonychus citri*)

The compounds of the present invention can be obtained in a high yield by reacting a carboxylic acid of the formula (II),

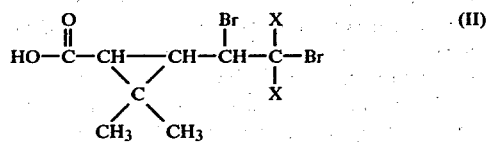

wherein X is as defined above, or its reactive derivative with an alcohol or its halide of the formula (III),

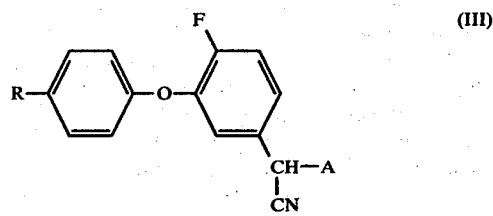

wherein R is as defined above and A is a hydroxyl group or a chlorine or bromine atom, or by reacting an aldehyde of the formula (IV),

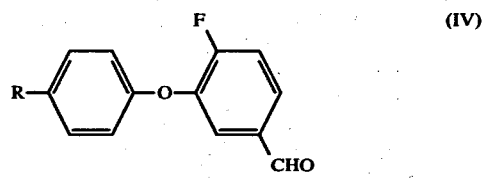

wherein R is as defined above, with a carboxylic halide of the formula (V),

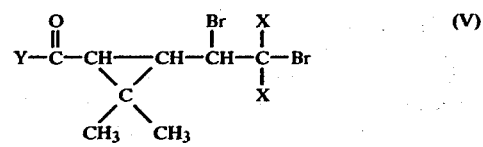

wherein X is as defined above and Y is a chlorine or bromine atom, and a sodium or potassium cyanide, or by brominating a carboxylic ester of the formula (VI),

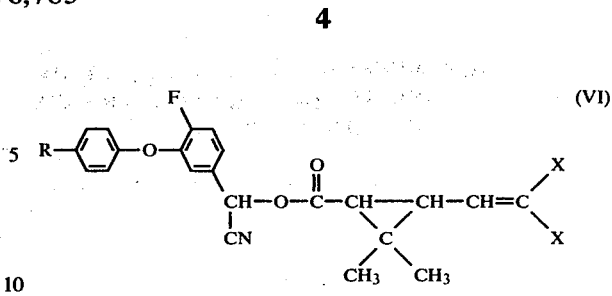

wherein R and X are as defined above with bromine. The reactive derivative of the carboxylic acid of the formula (II) referred to herein includes for example a carboxylic chloride, a carboxylic bromide, a carboxylic anhydride and a tertiary organic base salt, a potassium or sodium salt of the carboxylic acid.

The compounds of the present invention are also present as optical isomers based on the asymmetric carbon atoms of the alcohol and acid moieties. All these isomers are also included in the scope of the present invention.

Next, the outline of the production of the present carboxylic esters will be shown.

Synthesis A: Reaction between alcohol and carboxylic halide

The objective ester is obtained by reacting an alcohol of the formula,

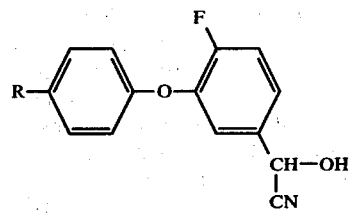

wherein R is as defined above, with a carboxylic halide of the formula,

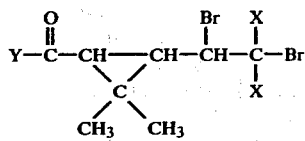

wherein X and Y are as defined above, preferably the acid chloride, at −30° C. to 100° C. for 0.5 to 10 hours in an inert solvent (for example, benzene, toluene, ether, hexane) in the presence of an acid-binding agent (for example, pyridine, triethylamine).

Synthesis B: Reaction between alcohol and carboxylic anhydride

The objective ester is obtained by reacting an alcohol of the formula,

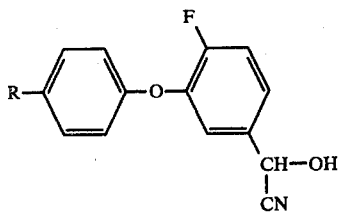

wherein R is as defined above, with a carboxylic anhydride of the formula,

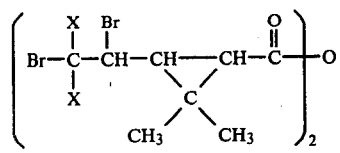

wherein X is as defined above, at −20° C. to 100° C. for 1 to 10 hours in an inert solvent (for example, benzene, toluene, hexane, acetone).

Synthesis C: Reaction between alcohol and carboxylic acid

The objective ester is obtained by reacting an alcohol of the formula,

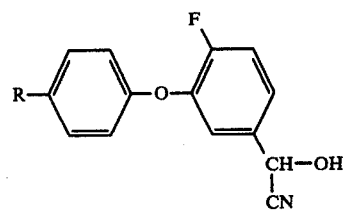

wherein R is as defined above, with a carboxylic acid of the formula,

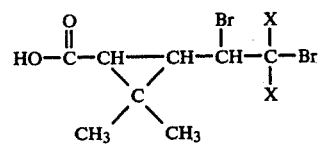

wherein X is as defined above, at 0° C. to 150° C. for 0.5 to 10 hours in an inert aolvent (for example, benzene, toluene, xylene) in the presence of a dehydration-condensing agent (e.g. dicyclohexylcarbodiimide).

Synthesis D: Reaction between halide and tertiary organic base salt of carboxylic acid The objective ester is obtained by reacting a halide of the formula,

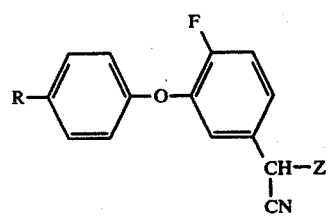

wherein R is as defined above and Z is a chlorine or bromine atom, with a carboxylic acid of the formula,

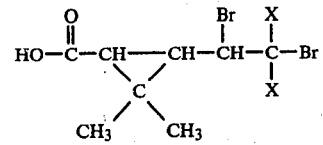

wherein X is as defined above, at 0° C. to 150° C. for 0.5 to 10 hours in an inert solvent (for example, acetone, benzene, dioxane) in the presence of a tertiary organic base (for example, triethylamine, trimethylamine).

Synthesis E: Reaction between halide and alkali metal salt of carboxylic acid

The objective ester is obtained by reacting a halide of the formula,

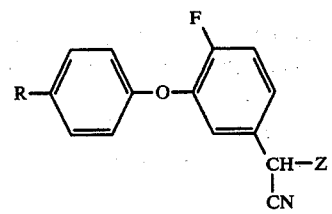

wherein R and Z are as defined above, with a sodium or potassium salt of a carboxylic acid of the formula,

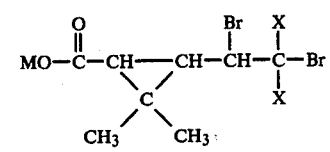

wherein X is as defined above and M is a sodium or potassium atom, at 0° C. to 150° C. for 0.5 to 10 hours in a two-phase system comprising water and an inert solvent (for example, toluene, heptane, benzene) in the presence of a phase transfer catalyst (for example, tetra-n-butylammonium bromide, benzyltriethylammonium chloride).

Synthesis F: Reaction among aldehyde, alkali metal cyanide and acid halide

F-1: The objective ester is obtained by reacting an aldehyde of the formula,

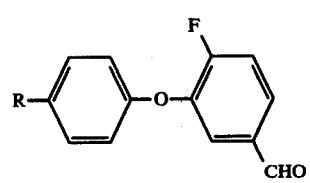

wherein R is as defined above, sodium cyanide or potassium cyanide and a carboxylic halide of the formula,

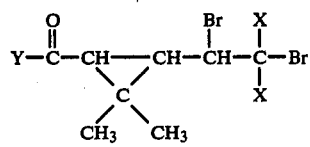

wherein X and Y are as defined above, at 0° C. to 150° C. for 0.5 to 20 hours in an inert solvent (for example, benzene, toluene) in the presence of a phase transfer catalyst (for example, dibenzo-18-crown-6, dicyclohexyl-18-crosn-6).

F-2: The objective ester is obtained by reacting an aldehyde of the formula,

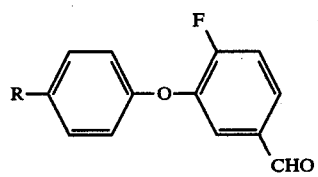

wherein R is as defined above, sodium cyanide or potassium cyanide and a carboxylic halide of the formula,

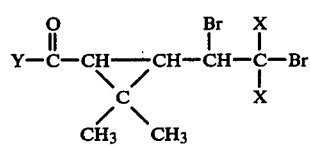

wherein X and Y are as defined above, at 0° C. to 100° C. for 0.5 to 10 hours in a two-phase system comprising water and an inert solvent (for example, benzene, hexane, toluene) in the presence of a phase transfer catalyst (for example, tetra-n-butylammonium bromide, benzyltriethylammonium chloride).

Synthesis G: Bromination of ester

The objective ester is obtained by reacting a carboxylic ester of the formula,

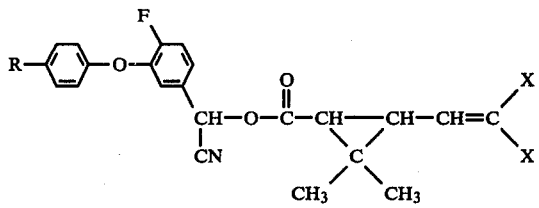

wherein R and X are as defined above, with bromine at −30° C. to 100° C. for 0.5 to 20 hours in an inert solvent (for example, carbon tetrachloride, methylene chloride, chlorobenzene).

The carboxylic esters of the present invention synthesized by the foregoing methods will be shown below.

| Compound No. | Structure and name | Refractive index or property |
|---|---|---|
| (1) | 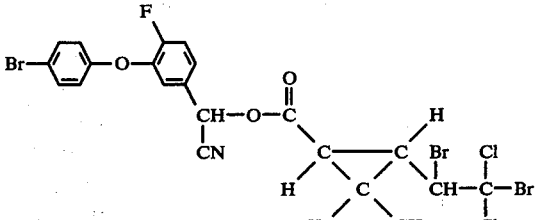 3-(4-Bromophenoxy)-4-fluoro-α-cyanobenzyl dl-trans-2,2-dimethyl-3-(1,2-dibromo-2,2-dichloroethyl)-cyclopropanecarboxylate | $n_D^{24.0}$ 1.5728 |
| (2) | 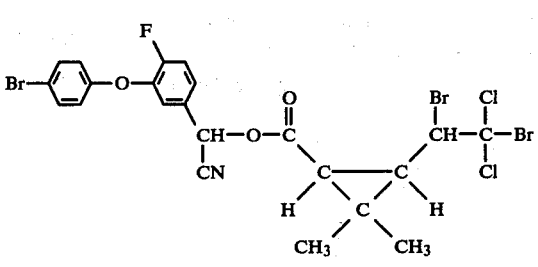 3-(4-Bromophenoxy)-4-fluoro-α-cyanobenzyl dl-cis-2,2-dimethyl-3-(1,2-dibromo-2,2-dichloroethyl)-cyclopropanecarboxylate | $n_D^{22.0}$ 1.5778 |

-continued

| Compound No. | Structure and name | Refractive index or property |
|---|---|---|
| (3) | 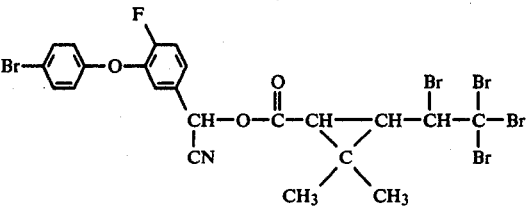<br>3-(4-Bromophenoxy)-4-fluoro-α-cyanobenzyl 2,2-dimethyl-3-(1,2,2,2-tetrabromoethyl)cyclopropanecarboxylate<br>[Mixture of a cis isomer (45%) and a trans isomer (55%)] | glassy oil |
| (4) | 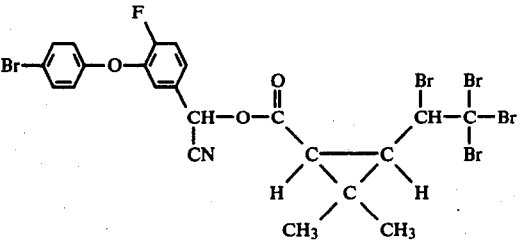<br>3-(4-Bromophenoxy)-4-fluoro-α-cyanobenzyl d-cis-2,2-dimethyl-3-(1,2,2,2-tetrabromoethyl)cyclopropanecarboxylate | glassy oil |
| (5) | 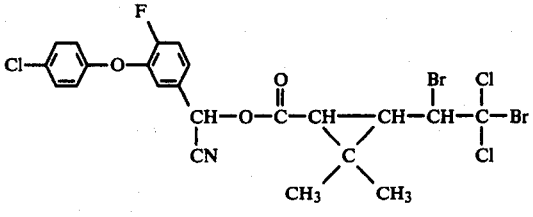<br>3-(4-Chlorophenoxy)-4-fluoro-α-cyanobenzyl 2,2-dimethyl-3-(1,2-dibromo-2,2-dichloroethyl)cyclopropanecarboxylate<br>[Mixture of a cis isomer (45%) and a trans isomer (55%)] | $n_D^{23.5}$ 1.5727 |
| (6) | 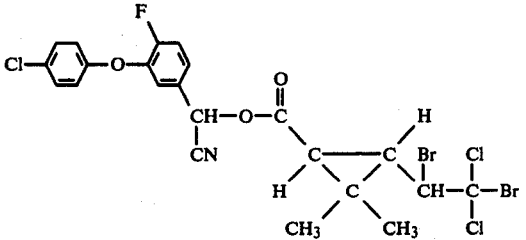<br>3-(4-Chlorophenoxy)-4-fluoro-α-cyanobenzyl dl-trans-2,2-dimethyl-3-(1,2-dibromo-2,2-dichloroethyl)-cyclopropanecarboxylate | $n_D^{24.0}$ 1.5735 |
| (7) | 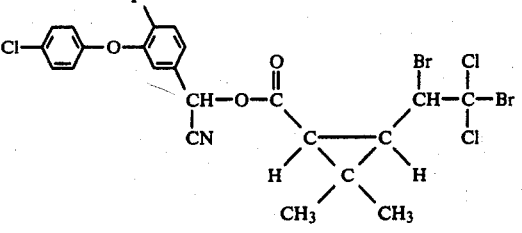<br>3-(4-Chlorophenoxy)-4-fluoro-α-cyanobenzyl dl-cis-2,2-dimethyl-3-(1,2-dibromo-2,2-dichloroethyl)-cyclopropanecarboxylate | $n_D^{22.0}$ 1.5750 |

| Compound No. | Structure and name | Refractive index or property |
|---|---|---|
| (8) | 3-(4-Chlorophenoxy)-4-fluoro-α-cyanobenzyl 2,2-dimethyl-3-(1,2,2,2-tetrabromoethyl)cyclopropane-carboxylate [Mixture of a cis isomer (45%) and a trans isomer (55%)] | glassy oil |
| (9) | 3-(4-Chlorophenoxy)-4-fluoro-α-cyanobenzyl d-trans-2,2-dimethyl-3-(1,2-dibromo-2,2-dichloroethyl)-cyclopropanecarboxylate | $n_D^{23.5}$ 1.5730 |
| (10) | 3-(4-Chlorophenoxy)-4-fluoro-α-cyanobenzyl d-cis-2,2-dimethyl-3-(1,2-dibromo-2,2-dichloroethyl)-cyclopropanecarboxylate. | $n_D^{23.5}$ 1.5752 |
| (11) | 3-(4-bromphenoxy)-4-fluoro-α-cyanobenzyl 2,2-dimethyl-3-(1,2-dibromo-2,2-dichloroethyl)-cyclopropanecarboxylate [Mixture of a cis isomer (45%) and a trans isomer (55%)] | $n_D^{23.5}$ 1.5782 |

The carboxylic esters obtained by the foregoing methods can be purified by chromatography or the like if necessary. The α-cyanobenzyl alcohol of the formula,

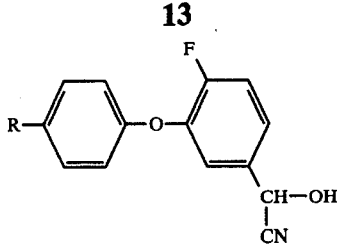

wherein R is as defined above, is easily obtained from the aldehyde of the formula (IV),

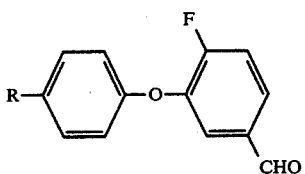

wherein R is as defined above, which can be synthesized according to examples 11 and 12, by the method described in "Preparative Organic Chemistry" (C. Hilgetag et al.) page 875. The halide of the formula,

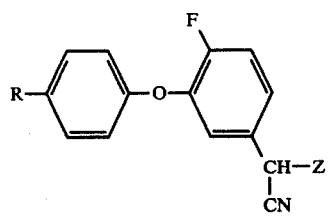

wherein R and Z are as defined above, is obtained from said alcohol and a halogenating agent (for example, phosphorus halide, thionyl chloride) by the method described in "Organic Synthesis" Col. Vol. III, page 793. The carboxylic acid of the formula (II),

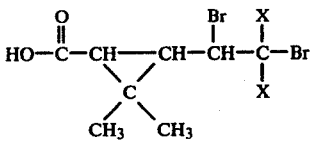

wherein X is as defined above, and carboxylic halide of the formula (V),

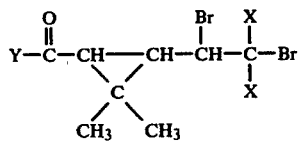

wherein X and Y are as defined above, can be obtained by the methods described in French Pat. No. 2398457 and Swiss Pat. No. 9347-77. Further, the carboxylic anhydride of the formula,

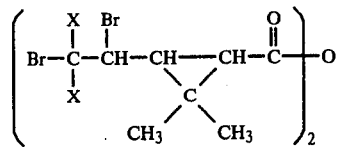

wherein X is as defined above, can be obtained in a good yield from these compounds by the method described in "Synthetic Organic Chemistry" (R. B. Wagner et al.) page 558.

The carboxylic ester used as a raw material can be obtained, for example, by the methods described in the following literature:

Elliott et al., Nature, 246, 169–170 (1973); 248, 710 (1974); British Pat. Nos. 1498931, 1498932, 1498933; U.S. Pat. Nos. 3,931,280, 3,842,125; Elliott et al., Pestic. Sci., 5, 791–799 (1974); Staudinger et al., Helv. Chem. Acta, 7, 390 (1924).

The synthesis of the present compounds and the intermediates for synthesizing them will be explained in more detail with reference to the following examples.

Example 1: Synthesis of the compound (1)

A solution of triethylamine (0.81 g, 8.0 mmole) in acetone (5 ml) was added dropwise to a solution of 3-(4-bromophenoxy-4-fluoro-α-cyanobenzyl bromide (2.31 g, 6.0 mmole) and dl-trans-2,2-dimethyl-3-(1,2-dibromo-2,2-dichloroethyl)cyclopropanecarboxylic acid (2.66 g, 7.2 mmole) in acetone (20 ml) at 15° C. to 20° C. with stirring. After the addition was finished, the reaction mixture was heated under reflux for 2 hours and allowed to cool. Triethylamine hydrobromide deposited from the reaction solution was filtered, and the filtrate was concentrated. The residue obtained was purified by column chromatography on silica gel to give 3.60 g of 3-(4-bromophenoxy)-4-fluoro-α-cyanobenzyl dl-trans-2,2-dimethyl-3-(1,2-dibromo-2,2-dichloroethyl)cyclopropanecarboxylate as a pale yellow liquid.

Example 2: Synthesis of the compound (2)

A solution of 3-(4-bromophenoxy)-4-fluorobenzaldehyde (1.48 g, 5.0 mmole) and dl-cis-2,2-dimethyl-3-(1,2-dibromo-2,2-dichloroethyl)cyclopropanecarboxylic chloride (2.03 g, 5.25 mmole) in toluene (10 ml) was added dropwise to a solution of sodium cyanide (0.37 g, 7.5 mmole) and benzyltriethylammonium chloride (0.25 g, 1.1 mmole) in water (5 ml) at room temperature with stirring. After the addition was finished, stirring was continued for 5 hours at the same temperature. The resulting solution was washed with sodium chloride-saturated water and dried over anhydrous sodium sulfate. The solvent was then removed by evaporation to give 3.10 g of 3-(4-bromophenoxy)-4-fluoro-α-cyanobenzyl dl-cis-2,2-dimethyl-3-(1,2-dibromo-2,2-dichloroethyl)cyclopropanecarboxylate as a pale yellow liquid.

Example 3: Synthesis of the compound (3)

A solution of 3-(4-bromophenoxy)-4-fluorobenzaldehyde (1.77 g, 6.0 mmole) and dl-cis.trans-2,2-dimethyl-3-(1,2,2,2-tetrabromoethyl)cyclopropanecarboxylic chloride (3.00 g, 6.3 mmole) in benzene (10 ml) was added dropwise to a suspension of sodium cyanide (0.44 g, 9.0 mmole) and dibenzo-18-crown-6 (0.1 g) in benzene (10 ml) at room temperature with stirring. After the addition was finished, stirring was continued overnight. The resulting solution was washed with sodium chloride-saturated water and concentrated. The residue obtained was purified by column chromatography on silica gel to give 4.25 g of 3-(4-bromophenoxy)-4-fluoro-α-cyanobenzyl dl-cis.trans-2,2-dimethyl-3-(1,2,2,2-tetrabromoethyl)cyclopropanecarboxylate as a pale yellow glassy oil.

Example 4: Synthesis of the compound (4)

A solution of bromine (1.06 g, 6.6 mmole) in carbon tetrachloride (5 ml) was added dropwise to a solution of 3-(4-bromophenoxy)-4-fluoro-α-cyanobenzyl dl-cis-2,2-dimethyl-3-(2,2-dibromovinyl)cyclopropanecarboxylate (3.61 g, 6.1 mmole) in carbon tetrachloride (20 ml) at 20° C. with stirring. After the addition was finished, stirring was continued overnight. The resulting solution was washed with a 10% aqueous sodium sulfite solution and then with sodium chloride-saturated water, dried over anhydrous sodium sulfate and concentrated. The residue obtained was purified by column chromatography on silica gel to give 4.20 g of 3-(4-bromophenoxy)-4-fluoro-α-cyanobenzyl d-cis-2,2-dimethyl-3-(1,2,2,2-tetrabromoethyl)cyclopropanecarboxylate as a pale yellow grassy oil.

Example 5: Synthesis of the compound (5)

A solution of dl-cis.trans-2,2-dimethyl-3-(1,2-dibromo-2,2-dichloroethyl)cyclopropanecarboxylic chloride (2.33 g, 6.0 mmole) in benzene (5 ml) was added dropwise to a solution comprising 3-(4-chlorophenoxy)-4-fluoro-α-cyanobenzyl alcohol (1.67 g, 6.0 mmole), benzene (10 ml) and pyridine (0.95 g, 12 mmole) with stirring while maintaining the temperature at 5° C. or less with ice-cooling. After the addition was finished, the reaction mixture was stirred overnight at room temperature, and separated into two layers with addition of water. The organic layer was washed with a 5% aqueous hydrochloric acid, sodium carbonate-saturated water and then with sodium chloride-saturated water, and then dried over anhydrous sodium sulfate. After removing the solvent by evaporation, the residue obtained was purified by column chromatography on silica gel to give 3.49 g of 3-(4-chlorophenoxy)-4-fluoro-α-cyanobenzyl dl-cis.trans-2,2-dimethyl-3-(1,2-dibromo-2,2-dichloroethyl)cyclopropanecarboxylate as a pale yellow liquid.

Example 6: Synthesis of the compound (6)

A solution of triethylamine (0.81 g, 8.0 mmole) in acetone (5 ml) was added dropwise to a solution of 3-(4-chlorophenoxy)-4-fluoro-α-cyanobenzyl bromide (2.04 g, 6.0 mmole) and dl-trans-2,2-dimethyl-3-(1,2-dibromo-2,2-dichloroethyl)cyclopropanecarboxylic acid (2.66 g, 7.2 mmole) in acetone (20 ml) at 15° C. to 20° C. with stirring. After the addition was finished, the reaction mixture was heated under reflux for 2 hours and allowed to cool. Triethylamine hydrobromide deposited from the reaction solution was filtered, and the filtrate was concentrated. The residue obtained was purified by column chromatography on silica gel to give 3.14 g of 3-(4-chlorophenoxy)-4-fluoro-α-cyanobenzyl dl-trans-2,2-dimethyl-3-(1,2-dibromo-2,2-dichloroethyl)cyclopropanecarboxylate as a pale yellow liquid.

Example 7: Synthesis of the compound (7)

A solution of 3-(4-chlorophenoxy)-4-fluorobenzaldehyde (1.25 g, 5.0 mmole) and dl-cis-2,2-dimethyl-3-(1,2-dibromo-2,2-dichloroethyl)cyclopropanecarboxylic chloride (2.03 g, 5.25 mmole) in toluene (10 ml) was added dropwise to a solution of sodium cyanide (0.37 g, 7.5 mmole) and benzyltriethylammonium chloride (0.25 g, 1.1 mmole) in water (5 ml) at room temperature with stirring. After the addition was finished, stirring was continued for 5 hours at the same temperature. The resulting solution was washed with sodium chloride-saturated water and dried over anhydrous sodium sulfate. The solvent was then removed by evaporation to give 2.80 g of 3-(4-chlorophenoxy)-4-fluoro-α-cyanobenzyl dl-cis-2,2-dimethyl-3-(1,2-dibromo-2,2-dichloroethyl)cyclopropanecarboxylate as a pale yellow liquid.

Example 8: Synthesis of the compound (8)

A solution of 3-(4-chlorophenoxy)-4-fluorobenzaldehyde (1.50 g, 6.0 mmole) and dl-cis.trans-2,2-dimethyl-3-(1,2,2,2-tetrabromoethyl)cyclopropanecarboxylic chloride (3.00 g, 6.3 mmole) in benzene (10 ml) was added dropwise to a suspension of sodium cyanide (0.44 g, 9.0 mmole) and dibenzo-18-crown-6(0.1 g) in benzene (10 ml) at room temperature with stirring. After the addition was finished, stirring was continued overnight. The resulting solution was washed with sodium chloride-saturated water and concentrated. The residue obtained was purified by column chromatography on silica gel to give 4.00 g of 3-(4-chlorophenoxy)-4-fluoro-α-cyanobenzyl dl-cis.trans-2,2-dimethyl-3-(1,2,2,2-tetrabromoethyl)cyclopropanecarboxylate as a pale yellow glassy oil.

Example 9: Synthesis of the compound (9)

A solution of sodium d-trans-2,2-dimethyl-3-(1,2-dibromo-2,2-dichloroethyl)cyclopropanecarboxylate (2.82 g, 7.2 mmole) and tetra-n-butylammonium bromide (0.081 g, 0.25 mmole) in water (10 ml) was added to a solution of 3-(4-chlorophenoxy)-4-fluoro-α-cyanobenzyl bromide (2.04 g, 6.0 mmole) in toluene (10 ml). The mixture was stirred at 70° C. to 80° C. for 4 hours. The resulting reaction solution was washed with sodium chloride-saturated water and dried over anhydrous sodium sulfate. The solvent was then removed by evaporation to give 3.13 g of 3-(4-chlorophenoxy)-4-fluoro-α-cyanobenzyl d-trans-2,2-dimethyl-3-(1,2-dibromo-2,2-dichloroethyl)cyclopropanecarboxylate as an orange liquid.

Example 10: Synthesis of the compound (10)

A solution of bromine (1.06 g, 6.6 mmole) in carbon tetrachloride (5 ml) was added dropwise to a solution of 3-(4-chlorophenoxy)-4-fluoro-α-cyanobenzyl d-cis-2,2-dimethyl-3-(2,2-dichlorovinyl)cyclopropanecarboxylate (2.81 g, 6.0 mmole) in carbon tetrachloride (20 ml) at 20° C. with stirring. After the addition was finished, stirring was continued overnight. The resulting solution was washed with a 10% aqueous sodium sulfite solution and then with sodium chloride-saturated water, dried over anhydrous sodium sulfate and concentrated. The residue obtained was purified by column chromatography on silica gel to give 3.05 g of 3-(4-chlorophenoxy)-4-fluoro-α-cyanobenzyl d-cis-2,2-dimethyl-3-(1,2-dibromo-2,2-dichloroethyl)cyclopropanecarboxylate as a pale yellow liquid.

Example 11: Synthesis of 3-(4-bromophenoxy)-4-fluorobenzaldehyde

A solution of bromine (9.60 g, 0.06 mmole) in methylene chloride (10 ml) was added dropwise to a solution of 3-phenoxy-4-fluorobenzaldehyde (10.8 g, 0.05 mmole) in methylene chloride (40 ml) at 20° C. taking a period of 1 hour with stirring. After the addition was finished, the reaction was continued for further 3 hours at the same temperature. The resulting solution was washed with water and then dilute aqueous potassium sulfite solution to remove the remaining bromine in the organic layer. The organic layer obtained was washed with a dilute aqueous sodium carbonate solution and then a dilute aqueous sodium chloride solution, and dried over anhydrous sodium sulfate and concentrated.

Yield of the residue: 14.50 g (98.3% of the theoretical amount)

And then, this residue was recrystallized from n-hexane/ethyl acetate mixture to give 12.5 g of crystal.
m.p.: 75.2° C.

Example 12: Synthesis of 3-(4-chlorophenoxy)-4-fluorobenzaldehyde

Dried sodium 4-chlorophenolate (14.0 g), which was prepared by reacting phenol (0.1 mmole) with sodium hydroxide (0.09 mmole) while removing the produced water as the toluene azeotrope, 3-bromo-4-fluorobenzaldehyde-diethylacetal (36.0 g), cuprous chloride (3.0 g) and N,N-dimethylformamide (100 ml) were put into a reaction vessel. The mixture was stirred at 140° C. to 150° C. under nitrogen stream for 15 hours. The resulting solution was allowed to cool and poured into a cold 15% aqueous hydrochloric acid solution followed by stirring for 30 minutes. And then, the resulting solution was extracted twice with ether. The ether layer was washed with an 1% aqueous sodium hydroxide solution and then an aqueous sodium chloride solution, and dried over anhydrous sodium sulfate. After removing ether by evaporation, the residue was distilled to give 16.2 g of 3-(4-chlorophenoxy)-4-fluorobenzaldehyde.

Yield: 72.0% of the theoretical amount
b.p.: 130°–145° C./0.2 mmHg
Refractive index: $n_D^{21.5}$ 1.5923

In the practical application of the present compounds obtained by the foregoing examples, the compounds may be applied alone without other components. Generally, however, they are formulated into preparations by blending with carriers for the ease of use as controlling agents and then diluted before use if necessary.

In producing the preparations of the present compounds, any one of the preparation forms such as emulsifiable concentrates, wettable powders, dusts, granules, fine granules, oil sprays, aerosols, heating fumigants (mosquito coils, electric mosquito killers), foggings, non-heating fumigants and baits, can be produced by the methods well known to those skilled in the art, with no need of particular conditions like the production of common agricultural chemicals. These preparations are applied to usages meeting the respective objects.

Further, a stronger insecticidal activity can be developed by blending two or more of these compounds. Also, the insecticidal activity of the present compounds can be increased by blending with synergists for pyrethroids, for example, α-[2-(2-butoxyethoxy)ethoxy]-4,5-methylenedioxy-2-propyltoluene (hereinafter referred to as piperonylbutoxide), 1,2-methylenedioxy-4-[2-(octylsulfinyl)propyl]benzene, 4-(3,4-methylenedioxyphenyl)-5-methyl-1,3-dioxane, N-(2-ethylhexyl)bicyclo-[2,2,1]hepta-5-2,3-dicarboximide, octachlorodipropyl ether and isoboronyl thiocyanoacetate.

The compounds of the present invention have a relatively high stability to light, heat and oxidation. If particularly necessary under severe oxidative conditions, however, a proper amount of stabilizer is blended with the present compounds. By this means, compositions of more stable effect can be obtained. The stabilizer includes for example antioxidants and ultraviolet absorbers such as phenol derivatives (for example, BHT, BHA), bisphenol derivatives, arylamines (for example, phenyl-α-naphthylamine, phenyl-β-napthylamine, condensation products of phenetidine and acetone), and benzophenone compounds.

Further, multi-purpose compositions of excellent efficacy can be produced by mixing with other active ingredients for example Allethrin, N-chrysanthemoxymethyl)-3,4,5,6-tetrahydrophthalimide (hereinafter referred to as tetramethrin), 5-benzyl-3-furylmethyl chrysanthemate (hereinafter referred to as resmethrin), 3-phenoxybenzyl chrysanthemate, 5-propargylfurfuryl chrysanthemate, 2-methyl-5-propargyl-3-furylmethyl chrysanthemate, d-trans or d-cis.trans isomers of the above chrysanthemates, pyrethrum extracts, d-trans or d-cis.trans chrysanthemic ester of d-allethrolone and other well-known cycloprpanecarboxylic esters; organophosphorus insecticides such as O,O-dimethyl O-(3-methyl-4-nitrophenyl)phosphorothioate (hereinafter referred to as Fenitrothion) and O,O-dimethyl O-(2,2-dichlorovinyl)phosphate (hereinafter referred to as Dichlorvos); carbamate series insecticides such as 1-napthyl N-methylcarbamate, 3,4-dimethylphenyl N-methylcarbamate, O-sec-butylphenyl N-methylcarbamate, O-iso-propoxyphenyl N-methylcarbamate, 3-methyl-4-diethylaaminophenyl N-methylcarbamate and 4-dimethylamino-3,5-xylylmethylcarbamate; other insecticides, fungicides, nematocides, acaricides, herbicides, plant growth reuglators, fertilizers, microbial insecticides [A.M. Helmpel et al., Insect Pathol, 1, 152 (1959)], insect hormone compounds and other agricultural chemicals. Further, a synergistic effect can be expected by such mixing.

The insecticidal and/or acsaricidal compositions according to this invention contain 0.01 to 80.0% by weight of an active ingredient.

Practical embodiments of the insecticidal or acaricidal composition according to this invention are illustratively shown in the following examples, wherein parts and percents are by weight.

Next, preparation examples of the insecticide and acaricide according to the present invention will be shown.

Preparation example 1

To 10 parts of each of the present compounds (1) to (11) are added 15 parts of Sorpol 3005 X (emulsifier, a mixture of nonionic and special anionic surfactants) and 75 parts of xylene. The mixture is thoroughly stirred to make a solution. An emulsifiable concentrate of each compound is thus obtained.

Preparation example 2

To 0.5 part of each of the present compounds (1) to (11) is added 0.3 part of PAP (isopropyl acid phosphate). The mixture is dissolved in 20 parts of acetone, and 99.2 parts of 300-mesh clay is added thereto. After thorough stirring, acetone is removed by evaporation to obtain a dust of each compound.

Preparation example 3

To 0.2 part of each of the present compounds (3), (5) and (9) are added 2 parts of m-tolyl N-methylcarbamate and then 0.3 part of PAP (described above). The mixture is dissolved in 20 parts of acetone, and 97.5 parts of 300-mesh clay is added thereto. After thorough stirring, acetone is removed by evaporation to obtain a dust of each compound.

Preparation example 4

Ten parts of each of the present compounds (1) to (11) is thoroughly mixed with 5 parts of Sorpol 3005 X, and 85 parts of 300-mesh diatomaceous earth is added thereto. The mixture is well mixed while being stirred in a mortar to obtain a wettable powder of each compound.

Preparation example 5

To 10 parts of each of the present compounds (3), (5) and (9) are progressively added 5 parts of 1-naphthyl N-methylcarbamate, 5 parts of Sorpol 3005 X and 80 parts of 300-mesh diatomaceous earth. The mixture is well mixed while being stirred in a mortar to obtain a wettable powder of each compound.

Preparation example 6

To 2 parts of each of the present compounds (1) to (11) are added 2 parts of sodium lignosulfonate (binder) and then 96 parts of clay (filler), and the mixture is well mixed while being stirred in a mortar. To the mixture is added water of 10% based thereon, and the mixture is well mixed with stirring, granulated by means of a granulator and air-dried to obtain a granule of each compound.

Preparation example 7

0.5 Part of each of the present compounds (1) to (11) is dissolved in kerosene and made up to 100 parts with kerosene to obtain an oil spray of each compound.

Preparation example 8

A mixture of 0.5 part of the present compound (5) and 2.5 parts of piperonylbutoxide is dissolved in kerosene and made up to 100 parts with kerosene to obtain an oil spray.

Preparation example 9

A mixture of 0.1 part of the present compound (5) and 0.2 part of Dichlorvos (described above) is dissolved in kerosene and made up to 100 parts with kerosene to obtain an oil spray.

Preparation example 10

0.4 Part of the present compound (5), 0.2 part of tetramethrin (described above), 7 parts of xylene and 7.4 parts of deodorized kerosene are well mixed to make a solution. The solution is filled in an aerosol container. After attaching a valve portion to the container, 85 parts of a propellant (liquefied petroleum gas) is charged therein through the valve under pressure to obtain an aerosol.

Next, an explanation will be given, with reference to the following examples, to show how suitable the present compounds are for controlling insects particularly to places wherein aquatic systems are present.

In order to know the pesticidal property of the compounds of the present invention, they were compared with the following compounds in Test Examples.

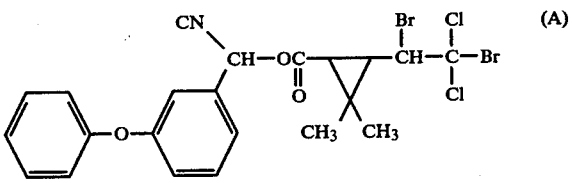

Compound disclosed in U.S. Pat. Nos. 4179575 and 4224227, and DT2805226.

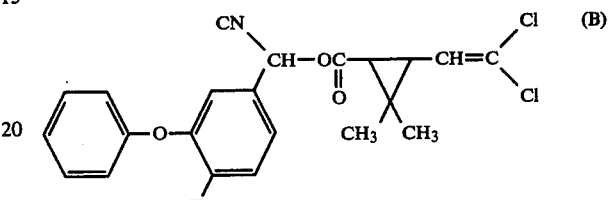

Compound disclosed in British Pat. Nos. 1549463, 1549462, 1565932 and 1565933.

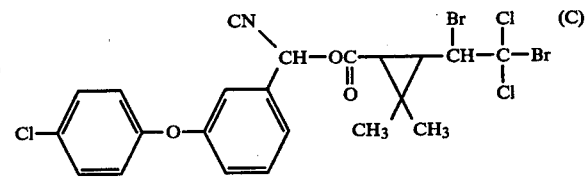

Compound disclosed in French Pat. Nos. 2380247 and 2380248.

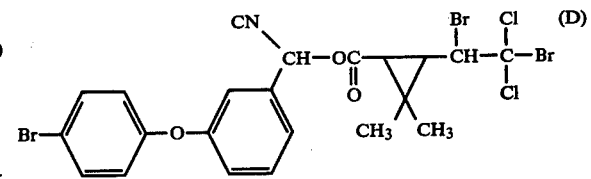

Compound disclosed in GB 2044765A.

Test example 1

Test method:

1. Test for toxicity to fishes

Toxicity to killifish (*Oryzias latipes*) was tested accordig to the test method for toxicity to fishes described in Notification B No. 2735 of the Ministry of Agriculture and Forestry (Nov. 25, 1965). Namely, each of the present compounds (1), (2), (4), (5), (6), (8), (9), (11) and reference compounds was dissolved or suspended in "Tween 80" and diluted successively with dechlorinated tap water. Ten killifish (0.2–0.3 g per fish) were released in a 10-liter glass vessel containing 5 liters of each preparation. After 48 hours, the dead and alive were observed to determine medium tolerance limit (48 hours) [TLm$_{48}$ (ppm)].

2 Test for insecticidal activity

The emulsifiable concentrates of the present compounds and reference compounds prepared in Preparation example 1 were each formulated into test solutions having four different concentrations of active ingredient between 500 ppm and 0.5 ppm. Each test solution was sprayed on a rice plant in a 180-ml plastic cup which had elapsed one month after sowing, at a rate of 15 ml/2 cups by means of a turn table. After air-drying, the rice plate was covered with a wire-screen cage, and 15 female adults of green rice leafhopper (*Nephotettix cincticeps*) (a strain resistant to carbamates and organophosphates, hereinafter referred to as R-strain) were liberated therein. The plant was placed in an artificial climate chamber kept at 26° C. After 24 hours, the dead and alive were examined. The median lethal concentratin [$LC_{50}$ (ppm)] was calculated from the mortality determined by 3 replications.

Result:

The toxicity to fishes and the insecticidal activity of the present compounds are shown in Table 1. In order to make it clearer that the present compounds have a low toxicity to fishes as well as a high insecticidal activity, a safety coefficient to fishes was calculated from the test results of toxicity to fishes and insecticidal activity.

$$\text{Safety coefficient to fishes} = \frac{\text{Toxicity of fishes } [TLm_{48} \text{ (ppm)}]}{\text{Insecticidal activity } [LC_{50} \text{ (ppm)}]}$$

A detailed explanation will be given to a method of how to calculate the safety coefficient. In the case of green rice leafhoppers, calculation was based on the concentration of active ingredient in water obtained by applying a test solution containing the active ingredient in an amount corresponding to $LC_{50}$ (ppm) to a flooded paddy field 5 cm deep at a rate of 100 liter/10 are, provided that all the active ingredient applied entered the water.

For example, the safety coefficient to fishes of the present compound (1) is calculated as follows: The quantity of water in a flooded paddy field 5 cm deep and 10 are in area is 50 tons; when a test solution containing the active ingredient in an amount corresponding to $LC_{50}$ (ppm) is added to the paddy field at a rate of 100 liter/10 are the concentration of the active ingredient in water (hereinafter referred to as (b)) is 0.008 pp; as the toxicity to fishes [$TLm_{48}$ (ppm)] (hereinafter referred to as (a)) is >2.0 ppm, said coefficient can be calculated by dividing (a) by (b). In this case, the coefficient is >250, which means that the present compound (1) has a safety higher than 250-fold.

TABLE 1

| Compound | Toxicity to fishes $TLm_{48}$ (ppm) (a) | Green rice leafhopper $LC_{50}$ (ppm) | Concentration of active ingredient in water (ppm)* (b) | Safety coefficient to fishes (a)/(b) |
|---|---|---|---|---|
| Present Compound | | | | |
| (1) | >2.0 | 3.8 | 0.008 | >250 |
| (2) | >2.0 | 6.0 | 0.012 | >167 |
| (4) | >2.0 | 6.3 | 0.013 | >154 |
| (5) | >1.0 | 4.8 | 0.010 | >100 |
| (6) | >1.0 | 2.7 | 0.005 | >200 |
| (8) | >1.0 | 5.8 | 0.012 | >83 |
| (9) | >1.0 | 1.5 | 0.003 | >333 |
| (11) | >2.0 | 4.7 | 0.010 | >200 |
| Reference Compound | | | | |
| (A) | 0.50 | 5.0 | 0.010 | 50 |
| (B) | <0.01 | 2.5 | 0.0005 | <2 |

*:The concentration of active ingredient in water obtained by applying a test solution containing the compound in an amount corresponding to $LC_{50}$ (ppm) to a flooded paddy field 5 cm deep at a rate of 1000 liter/10 are, provided that all the compound applied entered the water.

Text example 2

The emulsifiable concentrate of each of the present compounds (1) to (11) prepared in Preparation example 1 was diluted with water so that the concentration of active ingredient was 500 ppm. Five rice seedlings which had elapsed 10 days after sowing were dipped for 1 minute in the dilute solution and air-dried. The rice seedlings and 10 third instar larvae of rice stem borer (*Chilo suppressalis*) were placed in a plastic cup (diameter 5.5 cm, height 3.5 cm) which was then placed in an artificial climate chamber kept at 26° C. After 10 days, the dead and alive of the larvae were examined, and it was found that 100% of the larvae could be killed.

Text example 3

Fifty milligrams of each of the granules of the present compounds (5) and (11) obtained in Preparation example 6 was placed in a 100-ml beaker containing 100 ml of distilled water, and 30 full grown larvae of yellow fever mosquito (*Aedes aegypti*) were liberated therein. After 24 hours, 100% of the larvae could be killed.

Test example 4

The emulsifiable concentrate of each of the present compounds (3), (5), (9) and (11) prepared in Preparation example 1 was diluted with water so that the concentration of the active ingredient was 500 ppm. The dilute liquor was thoroughly sprayed on rice plants (grown in a 1/10,000 are Waner's pot) on which carmine mites (*Tetranychus cinnabarinus*) in all stages were made parasitic. After 10 days, the damage to rice plants by carmine mites was examined, and it was found that the spreading of the damage could be prevented in any case.

Text example 5

Residual effect test:

The emulsifiable concentrate of each of the present compounds (5) and (11) prepared in Preparation example 1 was diluted with water so that the conentration of active ingredient was 400 ppm. Thereafter, 20 cc of the dilute solution was sprayed on rice plants grown in a 1/10,000 are Wagner's pot. The rice plants were air-dried and covered with a wire-screen cage, and 15 female adults of green rice leafhopper (*Nephotettix cincticeps*) were liberated therein. After 24 hours, the dead and alive were examined to obtain mortality. In order to examine the residual effect, the pot was then left as it was for 7 days, and the test insects were liberated in the same manner as above. After 24 hours, the mortality was examined. The experiment was carried out in a greenhouse and the number of replications was three.

| Compound | Mortality (%) | |
|---|---|---|
| | Effect immediately after treatment | Effect 7 days after treatment |
| Present | | |
| compound No. (5) | 100 | 100 |
| compound No. (11) | 100 | 100 |
| Reference | | |
| compound MPMC* | 100 | 0 |
| Untreated | 0 | 0 |

*3,4-Xylyl N—methylcarbamate

Test example 6

The wettable powder of each of the present compounds (1), (3), (5), (6) and (11) prepared in Preparation example 4 was diluted with water so that the concentration of active ingredient was 100 ppm. Soil was placed in a plastic box [5 m×5 m×2 m (deep)] to a level of 50 cm from the bottom, and rice plants about 50 cm high were transplanted at invervals of 50 cm. Water was then placed in the box so that water depth was 5 cm, and 20 killifishes (Oryzias latipes) were liberated therein. Thereafter, the above dilute solution was sprayed on the box at a rate of 100 liter/10 are. The solution fell on the rice plants as well as on the water surface.

One hour after treatment, 100 female adults of green rice leafhopper (Nephotettix cincticeps) were liberated in the box which was immediately covered with a net. After 48 hours, no alive green rice leafhoppers were found, whereas all of the killifishes were alive.

Test example 7

The emulsifiable concentrate obtained in preparation Example 1 was diluted 200 times with water (corresponding to 500 ppm of the active ingredient). On the bottom a polyethylene cup of 5.5 cm in diameter was placed a piece of filter paper of the same size, and 0.7 ml of the above dilute liquor was dropped on the filter paper. Sucrose (30 mg) was placed on the paper as bait. Thereafter, 10 housefly female adults (Musca domestica) were liberated in the cup which was then covered with a lid. After 48 hours, the dead and alive were counted to obtain mortality (4 replications).

| Compound | Mortality (%) |
|---|---|
| Present compound | |
| (5) | 100 |
| (6) | 100 |
| (7) | 100 |
| (8) | 100 |
| (9) | 100 |
| (10) | 100 |
| Untreated | 0 |

Test example 8

The present compounds as below and reference compounds were each diluted with acetone into test solutions having four different concentrations of active ingredient. Each test solution was topically applied to the ventral throrax of CSMA strain housefly female adults (Musca domestica), at a rate of 0.5 µl/adult by means of a microapplicator.

The adults were then liberated in a polyethylene cup and fed with milk, sugar and water. After 24 hours, the dead and alive were observed. The median lethal dosage (LD$_{50}$ µg/adult) was obtained from the morality (3 replications).

| Compound | LD$_{50}$ µg/adult |
|---|---|
| Present compound | |
| (5) | 0.033 |
| (6) | 0.031 |
| (9) | 0.018 |
| (10) | 0.030 |
| Reference compound | |
| (C) | 0.062 |
| (D) | 0.063 |

What is claimed is:

1. A compound of the formula,

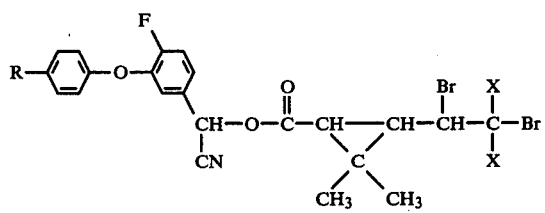

wherein R and X may be same or different, each is a chlorine or bromine atom.

2. A compound of the formula,

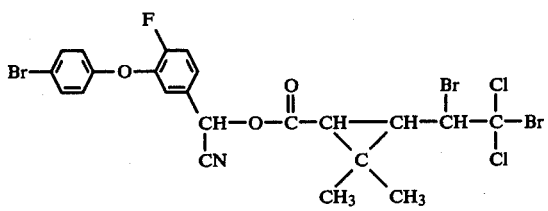

3. A compound of the formula,

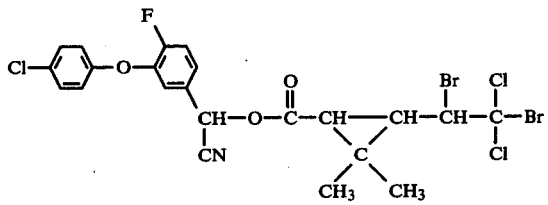

4. An insecticidal and/or acaricidal composition which comprises as an active ingredient an insecticidally and/or acaricidally effective amount of the compound according to claim 1 and an inert carrier.

5. A method for controlling an insect and/or acarid which comprises applying an insecticidally and/or acaricidally effective amount of the compound according to claim 1 to the insect and/or acarid.

6. The method according to claim 5, wherein the insect is those living in an aquatic place.

7. A compound of the formula,

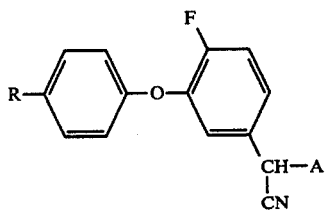
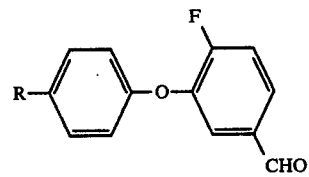
wherein R is a chlorine or bromine atom and A is a hydroxyl group or a chlorine or bromine atom.
8. A compound of the formula,
wherein R is a chlorine or bromine atom.
* * * * *